United States Patent [19]
Jensen et al.

[11] 3,944,978
[45] Mar. 16, 1976

[54] ELECTRO-OPTICAL METHOD AND APPARATUS FOR MAKING IDENTIFICATIONS

[75] Inventors: Niels P. Jensen, Los Angeles; Harvey L. Kasdan, Van Nuys; James T. Thomasson, Sunland, all of Calif.

[73] Assignee: Recognition Systems, Inc., Van Nuys, Calif.

[22] Filed: Sept. 9, 1974

[21] Appl. No.: 504,185

[52] U.S. Cl. 340/146.3 E; 340/146.3 P; 350/162 SF; 356/71
[51] Int. Cl.² ........................................ G06K 9/00
[58] Field of Search .............. 340/146.3 E, 146.3 P; 356/71; 350/162 SF

[56] References Cited
UNITED STATES PATENTS

| | | | |
|---|---|---|---|
| 3,619,060 | 11/1971 | Johnson | 340/146.3 E |
| 3,689,772 | 9/1972 | George et al. | 340/146.3 P |
| 3,701,098 | 10/1972 | Acker | 340/146.3 Z |
| 3,869,697 | 3/1975 | Kawasaki | 340/146.3 P |
| 3,873,970 | 3/1975 | McMahon et al. | 340/146.3 E |

*Primary Examiner*—Leo H. Boudreau
*Attorney, Agent, or Firm*—Ralph B. Pastoriza

[57] ABSTRACT

A reference diffraction pattern is generated by radiating an invariant physical characteristic such as a fingerprint with coherent light, this reference diffraction pattern being converted by a detector into a reference electrical function which is stored. A person to be identified then has a corresponding invariant physical characteristic such as his fingerprint radiated by coherent light to cause generation of a sample diffraction pattern. The frequency domain of the entire sample diffraction pattern is detected simultaneously to provide a sample electrical function. The reference electrical function in storage is then compared with the sample electrical function and if a correlation exists within a given tolerance, it is known that the person from which the sample electrical function is derived corresponds to the person from which the reference electrical function was derived. The invariant physical characteristics may be fingerprints as mentioned, or signatures, or combinations of both.

8 Claims, 3 Drawing Figures

ELECTRO-OPTICAL METHOD AND APPARATUS FOR MAKING IDENTIFICATIONS

This invention relates generally to electro-optical recognition techniques and more particularly to an improved method and apparatus for making identifications by the generation of diffraction patterns.

BACKGROUND OF THE INVENTION

Many systems have been proposed heretofore for verifying identifications by analyzing an invariant physical characteristic of a person such as his fingerprint. Some of these techniques involve an examination of the image of the fingerprint by irradiating the same with light. The image formation can be filtered in terms of frequencies and compared with similar stored information in a spatial domain.

In other systems, a light diffraction pattern is generated from a person's fingerprint and an electrical function of the detected diffraction pattern is derived. The technique for deriving the electrical function of the diffraction pattern involves a mechanical scanning of the diffraction pattern so that electrical information is derived in series; that is, the electrical function is continuously generated over a period of time corresponding to the time necessary to complete the scanning of the pattern. Again this electrical function can be compared with a stored electrical function to determine if a proper correlation exists and thereby verify the identity of a person.

The reliability and accuracy of any specific identification or verification carried out by the aforementioned prior art arrangements depends on the total amount of information that can be derived for comparison with the stored information. In other words, the derived electrical function from an image or a diffraction pattern of a person's fingerprint is more reliable the more data there is contained in the electrical function.

BRIEF DESCRIPTION OF THE PRESENT INVENTION

The present invention has as its primary object the provision of an improved method and apparatus for making identifications or verifications utilizing many of the techniques discussed above in the prior art but wherein substantially better information and data is detected for comparison with a corresponding amount of data which is stored so that greatly increased reliability and accuracy in carrying out identifications are realized.

Briefly, the method and apparatus of the present invention contemplates storing a reference electrical function corresponding to a reference diffraction pattern formed by radiating with coherent light an invariant physical reference characteristic of a given person. A corresponding invariant physical characteristic of a person to be identified is then radiated by coherent light to cause generation of a sample diffraction pattern of this characteristic. The frequency domain of the entire sample diffraction pattern is then simultaneously detected to provide a sample electrical function thereof. The reference electrical function is then compared with the sample electrical function such that if a correlation exists within a given tolerance, it is known that the person from which the sample electrical function is derived corresponds to the given person from which the reference electrical function was generated.

The invariant physical characteristics involved may constitute fingerprints, signatures or other samples of handwriting, or in specific embodiments of the present invention combinations of such characteristics.

An essential feature of the present invention is the simultaneous detection of the entire diffraction patterns involved, the total information being taken out in parallel as opposed to a scanning technique which results in a series type generation of the electrical function. The results of the techniques of the present invention, as stated, provide for substantially better data which can be utilized in making comparisons so that increased reliability and accuracy in the verification process are realized.

BRIEF DESCRIPTION OF THE DRAWINGS

A better understanding of the present invention will be had by now referring to the accompanying drawings in which.

DETAILED DESCRIPTION OF THE PREFERRED EMBODIMENT

Figure 1:
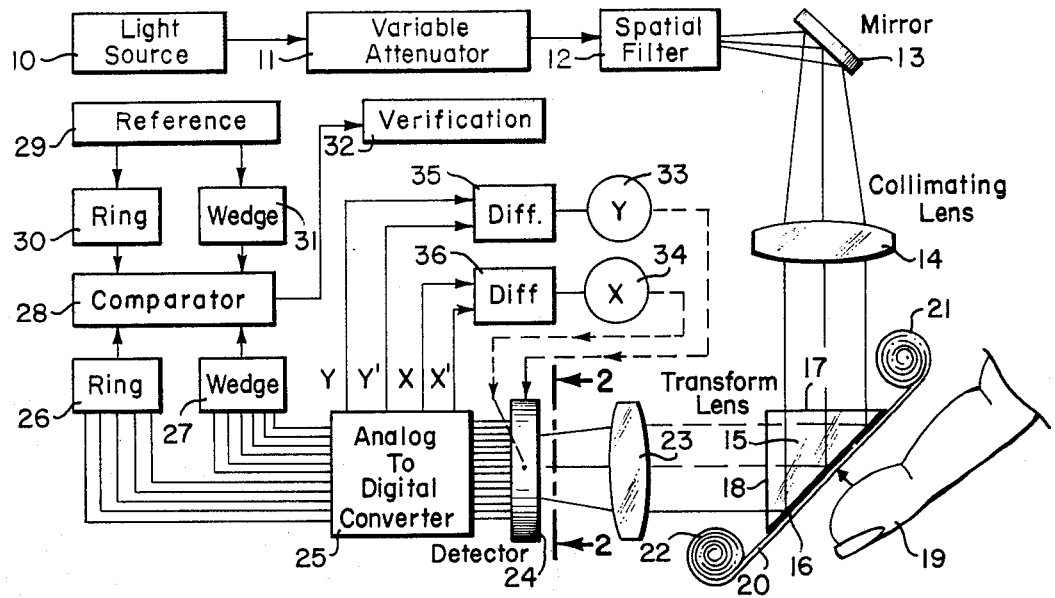
FIG. 1 is a schematic block diagram of the identification system of this invention.

Referring to FIG. 1, the electro-optical system for making identifications includes a light source 10 which preferably constitutes a coherent light generator such as a laser. As shown, coherent light from the source 10 may be passed through a variable light attenuator 11, spatial filter 12 to a mirror 13. From the mirror 13, the coherent light passes through a collimating lens 14 and to a prism 15 having its diagonal surface 16 disposed at right angles to the beam as shown. With this arrangement, the coherent light will enter one side 17 of the prism and be internally reflected from the diagonal surface 16 and thence exit from the other side 18.

An invariant physical characteristic such as a fingerprint from a person's finger 19 is arranged to be irradiated by the coherent light. Towards this end and in the particular embodiment illustrated, there is provided a transparent film 20 positioned against the exterior diagonal surface of the prism shown at 16 in such a manner that a person may impress his finger-print against the film, the coherent light being internally reflected from the diagonal surface 16 defining a diffraction pattern of the fingerprint. In the embodiment shown, the film 20 may be moved as by rotating supply and take up spools 21 and 22 to position a fresh portion of film over the exterior diagonal surface of the prism preparatory to receiving another finger print for irradiation by the coherent light.

The light diffraction pattern developed by the swirls of the fingerprint exits from the other side of the prism 18 as described, the same passing through a transform lens 23 to a detecting means in the form of a solid state detector 24.

The solid state detector 24 constitutes an important component in the combination of the present invention. This detector is made up of a plurality of segments each of which simultaneously detects portions of the diffraction pattern falling thereon so that in essence the frequency domain of the entire diffraction pattern is detected simultaneously and passed to an analog to digital converter 25.

As will become clearer as the description proceeds, the plurality of segments include semi-circular ring segments circumferentially extending over half of the solid state detector surface and wedge segments radially extending on the other half of the surface. There are thus two sets of signals developed corresponding respectively to the ring segment detectors and the wedge segment detectors. These signals are referred to herein for convenience as ring signals and wedge signals and, as shown, are separately processed in blocks 26 and 27 of FIG. 1.

The ring and wedge signals make up a sample electrical function representative of the sample diffraction pattern provided by a person's finger 19. This sample electrical function is passed to a comparator 28 for comparison with a reference electrical function stored in reference block 29.

In the preferred embodiment described, the stored reference electrical function is derived from a reference diffraction pattern of a given person's fingerprint. This reference diffraction pattern is detected in the same manner as described for the sample diffraction pattern in that ring and wedge signals are segregated as indicated by the blocks 30 and 31 prior to being passed into the comparator 28.

The comparator 28 effects a correlation of the sample ring signals from block 26 and the reference ring signals from block 30. Also carried out is a cross-correlation between the sample wedge signals from block 27 and the reference wedge signals from block 31. The correlation and cross-correlation techniques provide an overall correlation of the sample electrical function and reference electrical function which is rotationally invariant. In other words, should the sample diffraction pattern be rotated as a consequence of a person not positioning his figerprint 19 in a given rotational orientation, the results of the ultimate correlation will not vary.

As shown in FIG. 1, there is provided a verification indicator shown by block 32 which will indicate a proper identification or verification if the correlation of the sample and reference electrical functions falls within a given tolerance. If the correlation result falls outside the given tolerance, the verification block 32 will indicate that the person's fingerprint is not the same fingerprint as stored in the reference 29.

When a person impresses his finger against the film 20 bearing against the exterior diagonal surface 16 of the prism 15, the slight pressure can cause optical misalignment such that the generated diffraction pattern will not always be properly centered with respect to the surface of the solid state detector 24. In order that a consistent centering will be assured, there is provided a servo mechanism for automatically positioning the detector to a centered position relative to the generated diffraction pattern.

Thus, as illustrated in FIG. 1 there are provided Y and X servo motors 33 and 34 capable of physically translating the solid state detector 24 in a vertical or horizontal direction or a combinatiion of both directions. The surface of the detector 24 includes a centered ring with separate conductors attached to each of the four quadrants from which signals are derived which will indicate any error as a consequence of off-centering of the diffraction pattern relative to the detector. These signals are passed from the analog to digital converter 25 through suitable differential amplifiers 35 and 36 to control the Y and X servos 33 and 34 in a manner to recenter detector 24 relative to the diffraction pattern.

Figure 2:
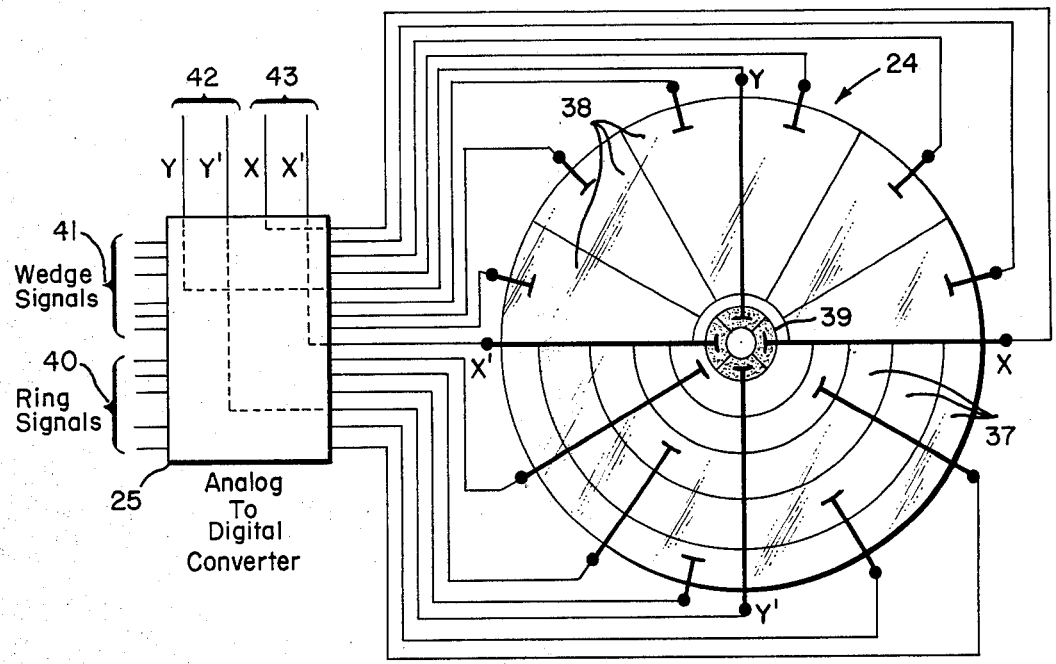
FIG. 2 is a front view of the solid state detector portion of the circuit of FIG. 1 looking in the direction of the arrows 2—2; and, FIG. 3 illustrates a modified arrangement in the optical portion of the system for enabling additional input information to be provided to the detector.

FIG. 2 illustrates the front face of the solid state detector 24 wherein some of the foregoing described features will become clearer. Thus, the various semi-circular circumferentially extending ring shaped segments are shown at 37 on the lower half of the detector surface while the radially extending wedge segments are shown at 38 on the upper half of the surface.

The centered ring for providing centering signals to the servo motors described in FIG. 1 is shown at 39 and as indicated, comprises four equal segments.

Electrical connections to the various semi-circular ring segments, radially extending wedge segments, and the equal segments making up the cenered ring 39 are indicated by the heavy lines terminating in small arcs. In an actual embodiment, these electrical connections would include equal potential conductors extending circumferentially over the ring segments and radially over the wedge segments so that maximum signal pick-up would be realized.

In FIG. 2, the various ring signals are indicated on conductors 40 extending from the analog to digital converter 25 while the various wedge signals are indicated on conductors 41 similarly extending from the block 25 as described in FIG. 1. The centering signals from the four segments of the ring 39 are detected by the conductors designated X', Y, X and Y'. These conductors similarly pass into the analog to digital converter block 25 and are passed therefrom as the Y direction and X direction centering signals on lines designated 42 and 43 respectively.

Figure 3:
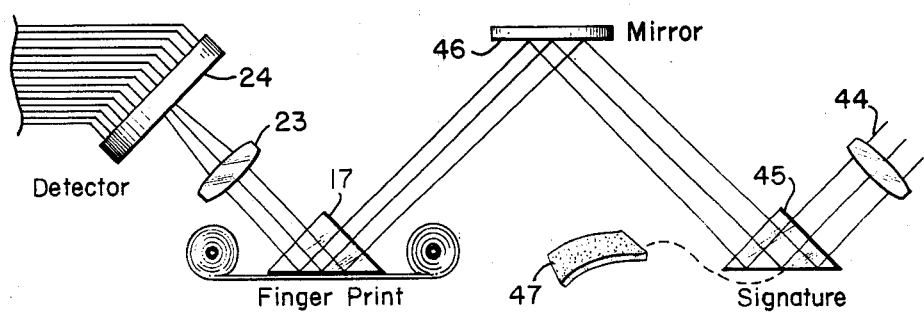

Referring now to FIG. 3, there is shown a modified arrangement in the optical system for providing further information to be used in effecting an identification or verification. Thus, the coherent light may be passed through an additional prism 45 having a diagonal surface against the exterior of which may be provided an additional invariant physical characteristic such as a person's signature. The developed diffraction pattern of this characteristic passes to a mirror 46 and then continues through the prism 17 where the light is further disturbed by the person's finger-print prior to passing through the transform lens 23 to the solid state detector 24 as described in FIG. 1.

In utilizing a person's signature or handwriting, it is convenient to employ a film strip such as indicated at 47 in FIG. 3 provided with an adhesive surface to hold the film against the exterior of the diagonal surface of the prism 45. A person may then simply write his signature on the film and after the same has been irradiated by coherent light to form the diffraction pattern, the film strip 47 can simply be peeled from the surface. The adhesive material in turn will pull any particles or the like from the prism surface to maintain it in a clean condition.

The foregoing arrangement is similar to the use of the film described with respect to the prism 17 in maintaining the surface of the prism clean. It merely represents an alternative arrangement. In this respect, another means for positioning a physical characteristic such as a person's signature for proper irradiation would be to cover the exterior diagonal surface of the prism with a film and trace impression material similar to the well known "magic slate" used by children. Once the signature has been impressed and properly irradiated, the outer film surface could be lifted to completely erase the signature preparatory to receiving another signature for identification.

It should be understood with respect to the foregoing that in utilizing a single prism such as described in FIG. 1 either a fingerprint or signature could be used. In the system of FIG. 3 both a fingerprint and signature are indicated as being used to provide a detailed combination diffraction pattern which contains substantially more information than would result from either diffraction pattern considered separately. Comparison of this combination diffraction pattern with a similarly stored diffraction pattern would increase substantially the accuracy of a verification or identification.

Another advantage of the arrangement shown in FIG. 3 is the ability of the system to effect an identification or verification of two separate persons. For example, if access to a given secret area were only permitted to two individuals simulaneously proper identification of such individuals could be readily realized by having each place his fingerprint on one of the individual prisms shown in FIG. 3 so that the final diffraction pattern passed to the detector would constitute a combination of the diffraction pattern of one person's fingerprint with that of the other. Having a similar combination diffraction pattern stored in the system would enable a verification to be effected.

OPERATION

The operation of the identification system will be evident from the foregoing description. Thus, it will be understood with reference to FIG. 1 that there is initially stored in the reference block 29 a reference electrical function derived from a reference diffraction pattern made of a person's fingerprint or other invariant physical characteristic. If a person claims to be the same as the given person whose characteristic is stored in the reference 29 a verification of such identy is accomplished by having him simply press his fingerprint on the exterior diagonal surface on the prism 15. This fingerprint is then irradiated with light from the light souce 10 as described to develop a diffraction pattern which is detected by the detector 24.

The various ring and wedge signals develop then pass to the comparator as described heretofore for comparison with the ring and wedge signals from the reference 29. A high degree of correlation falling within a given tolerance will then activate the verification block 32 to show that the person whose sample diffraction pattern has been detected corresponds to the given person whose diffraction pattern is in the reference storage 29. If the correlation falls outside the given tolerance, the verification block 32 will indicate that the person is not the same as the given person whose diffraction pattern has been stored.

As also described heretofore, by correlating the ring reference and sample signals and cross-correlating the wedge reference and sample signals, the overall correlation is rotationally invariant so the particular angular orientation that the person positions his finger relative to the prism surface will not change the result. Moreover, and as also described briefly heretofore, the pressure the person excerts which might cause optical misalignment of the developed diffraction pattern relative to the detector surface 24 will not affect the accuracy of the final verification because of the automatic centering means provided by the servo motors. Thus, if there is an off-centering of the detector relative to the diffraction pattern, there will be a difference in the Y and Y' signals which difference will operate the servo motor 33 to translate the detector in a Y direction towards a proper center position. Similar error signals will be developed in the X direction. When the detector has been properly centered, the signals from the various centered ring segments will all be equal and the servo motors will stop.

By the use of the particular solid state detector as described, all of the information in the diffraction pattern is taken out simultaneously, that is, in parallel. Thus, complicated mechanical scanning systems and the like are avoided.

It should be understood that while only a few semicircular segments and radially extending wedges have been shown in FIG. 2, in an actual embodiment there would be a substantially greater number of these segments.

Also, while only one additional prism has been illustrated in FIG. 2 it should be understood that further prisms could be incorporated to provide a combination of several different diffraction patterns of various unique invariant physical characteristics to thereby further increase the reliability and accuracy in effecting proper identifications.

The invention, accordingly, is not to be thought of as limited to the specific embodiments set forth merely for illustrative purposes.

What is claimed is:

1. A method of verifying a person's identity comprising the steps of:
    a. storing a reference electrical function corresponding to a reference diffraction pattern formed by radiating with coherent light an invariant physical reference characteristic of a given person by detecting the referenced diffraction pattern by means of a solid state detector made up of semi-circular ring segments and radially extending wedge segments to provide ring reference signals and wedge reference signals simultaneously;
    b. positioning an invariant physical sample characteristic of a person for radiation by coherent light to cause generation of a sample diffraction pattern of said characteristic;
    c. detecting the frequency domain of the entire sample diffraction pattern simultaneously to provide a sample electrical function thereof by means of a solid state detector made up of semi-circular ring segments and radially extending wedge segments to provide ring sample signals and wedge sample signals simultaneously;
    d. maintaining said solid state detector centered relative to said sample diffraction pattern by providing means on said solid state detector for generating error signals in response to an off-centering of the diffraction pattern and utilizing the error signals to center said solid state detector to assure that the same conditions exist as when said referenced diffraction pattern was detected; and
    e. comparing said reference electrical function to said sample electrical function by correlating the reference and sample ring signals together and cross-correlating the reference and sample wedge signals together so that the resulting correlation is rotationally invariant whereby if a correlation exists within a given tolerance it is known that the person from which the sample electrical function is derived corresponds to said given person.

2. The method of claim 1, in which said invariant physical characteristic constitutes a fingerprint.

3. The method of claim 1, in wich said invariant physical characteristic constitutes handwriting.

4. The method of claim 1, in which said invariant physical characteristic constitutes a combination of a finger-print and handwriting.

5. An apparatus for verifying a person's identity comprising, in combination:
   a. a coherent light source;
   b. positioning means for positioning an invariant physical characteristic of a person to be identified for radiation by coherent light from said source to form a sample diffraction pattern of said physical characteristic;
   c. detector means comprising a solid state detector made up of a plurality of segments arranged to define semi-circular ring shaped segments circumferentially extending over one half the surface of said solid state detector and wedge shaped segments radially extending over the other half of said surface upon which said entire diffraction pattern is projected to provide simultaneously ring sample signals and wedge sample signals constituting a sample electrical function of said sample diffraction pattern;
   d. centering means including a central ring in said solid state detector with four conductors attached respectively to each of four quadrants of the ring; servo means for translating said solid state detector; and centering signal detecting means responsive to signals generated in said conductors connected to said servo means and responsive to error signals resulting from an off-centering of said solid state detector relative to said sample diffraction pattern for energizing said servo means to recenter said solid state detector; and
   e. comparator means receiving said sample electrical function for comparison with a stored reference electrical function including ring reference signals and wedge reference signals derived in a similar manner from a given person, said comparator means correlating the sample and reference ring signals together and cross-correlating the sample and reference wedge signals together so that the resulting correlation is rotationally invariant, and providing a verification signal if a correlation of said sample electrical function with said reference electrical function exists within a given tolerance.

6. An apparatus according to claim 5, in which said positioning means includes at least one right angle prism; and film means in surface contact with the exterior diagonal surface of said prism, said invariant physical characteristic being impressed against the exterior of said film means, coherent light from said source entering one side surface of the prism to internally reflect from said diagonal surface and pass out the other side surface of the prism for detection by said solid state detector, whereby after a diffraction pattern has been generated and detected, said film means may be moved to position a fresh film portion against the exterior diagonal surface of the prism preparatory to receiving a next invariant physical characteristic whereby said exterior diagonal surface of the prism is kept clean.

7. An apparatus for verifying a person's identity comprising, in combination:
   a. a coherent light source;
   b. positioning means for positioning an invariant physical characteristic of a person to be identified for radiation by coherent light from said source to form a sample diffraction pattern of said physical characteristic;
   c. detector means comprising a solid state detector made up of a plurality of segments upon which said entire diffraction pattern is projected to provide simultaneously a plurality of signals constituting a sample electrical function of said sample diffraction pattern; and
   d. comparator means receiving said sample electrical function for comparison with a stored reference electrical function derived in a similar manner from a given person, said comparator means providing a verification signal if a correlation of said sample electrical function with said reference electrical function exists within a given tolerance said positioning means including at least one right angle prism with film means in surface contact with the exterior diagonal surface of the prism, said invariant physical characteristic being impressed against the exterior of said film means, coherent light from said source entering one side surface of the prism to internally reflect from the diagonal surface and pass out the other side surface of the prism for detection by said solid state detector, whereby after a diffraction pattern has been generated and detected, said film means may be moved to position a fresh film portion against the exterior diagonal surface of the prism preparatory to receiving a next invariant physical characterstic so that the external diagonal surface of the prism is kept clean, and an additional right angle prism with its exterior diagonal surface spaced from the exterior diagonal surface of the first mentioned prism, said coherent light passing through said additional right angle prism prior to entering said first mentioned prism whereby an additional invariant physical characteristic may be positioned for detection relative to said additional prism to provide a sample diffraction pattern combining both of said physical characteristics.

8. An apparatus according to claim 7, including a transparent film with an adhesive surface positioned against the exterior diagonal surface of said additional prism for receiving said additional invariant physical characteristic, said film then being peeled from said exterior diagonal surface, the adhesive thereon pulling free any particles so that said additional diagonal surface is maintained clean.

* * * * *